United States Patent [19]

Manning

[11] 4,067,924

[45] * Jan. 10, 1978

[54] DEHYDROGENATION PROCESS

[75] Inventor: Harold E. Manning, Houston, Tex.

[73] Assignee: Petro-Tex Chemical Corporation, Houston, Tex.

[*] Notice: The portion of the term of this patent subsequent to Dec. 25, 1990, has been disclaimed.

[21] Appl. No.: 713,160

[22] Filed: Aug. 10, 1976

Related U.S. Application Data

[60] Division of Ser. No. 540,334, Jan. 13, 1975, abandoned, which is a division of Ser. No. 475,608, June 3, 1974, Pat. No. 3,960,975.

[51] Int. Cl.$^2$ .......................... C07C 3/28; C07C 5/18; C07C 5/32; C07C 5/42
[52] U.S. Cl. .............................. 260/683.3; 260/669 R
[58] Field of Search .................. 252/468; 260/680 G, 260/680 R, 669 R, 683.3

[56] References Cited

U.S. PATENT DOCUMENTS

| | | | |
|---|---|---|---|
| 2,205,140 | 6/1940 | Heard | 260/683 |
| 2,205,141 | 6/1940 | Heard | 260/683 |
| 2,209,453 | 7/1940 | Heard et al. | 260/683 |
| 3,767,596 | 10/1973 | Manning | 252/468 |
| 3,781,376 | 12/1973 | Manning | 260/683.3 |
| 3,801,672 | 4/1974 | Bajars | 260/683.3 |
| 3,925,498 | 12/1975 | Stadig | 260/683.3 |

Primary Examiner—O. R. Vertiz
Assistant Examiner—Eugene T. Wheelock
Attorney, Agent, or Firm—Kenneth H. Johnson

[57] ABSTRACT

Magnesium chromites promoted with aluminum have been found to be superior to chromia-alumina type dehydrogenation catalysts, for example, in the dehydrogenation of n-butane. The aluminum is either added to the preformed magnesium chromite or is incorporated into the spinel structure of the chromite itself or added in both ways. The aluminum will be present in the catalyst from all sources in an atomic ratio of Al:Cr of 0.0004 to 1.2:1. The atomic ratio will more usually be 0.04 to 0.8:1, Al:Cr.

3 Claims, No Drawings

DEHYDROGENATION PROCESS

This is a continuation, of application Ser. No. 540,334 filed Jan. 13, 1975, now abandoned which is a division of Ser. No. 475,608, filed June 3, 1974, now U.S. Pat. No. 3,960,975.

This invention relates to a process for the dehydrogenation of gaseous hydrocarbons and the catalyst employed. More specifically the process is a cyclic process wherein there are alternating cycles of dehydrogenation and catalyst regeneration.

The process is a cyclic process in which gaseous hydrocarbons such as butane or isopentane are dehydrogenated over a suitable catalyst to produce butenes and butadiene and isopentene and isoprene respectively. After each dehydrogenation cycle there is a catalyst regeneration cycle in which the accumulated coke is burned off by passing molecular oxygen through the catalyst followed by another dehydrogenation cycle and so on.

The chromia-alumina catalysts have been recognized for a number of years as the most preferred catalyst for this type of process. The chromia-alumina catalysts are prepared by treating activated alumina with a solution of chromic acid, draining off the excess acid from the alumina, drying and heat treating at about 1400° F. Commercial chromia-alumina dehydrogenation catalysts normally contain about 20% chromium oxide. Preparative methods are shown, for example, in U.S. Pat. Nos. 2,399,678 and 2,419,997.

Other chromia-metal oxide materials have been investigated for their dehydrogenation capabilities. One of the more prominent among these has been chromia-magnesia which has been found to be a poor second to chromia-alumina. Several patents were issued to Tropsch in the late 1930's relating to magnesia based chromia dehydrogenation catalysts, e.g., U.S. Pat. Nos. 2,122,786; 2,122,787; 2,122,790; and 2,148,140. Pitzer disclosed chromia-magnesia-alumina dehydrogenation catalyst in U.S. Pat. No. 2,638,455.

It is an object of the present invention to find an alternative catalyst to chromia-alumina for use in cyclic dehydrogenation processes. It is another object of the present invention to find a catalyst superior to the chromia-alumina catalysts for use in dehydrogenation. It is still a further object to provide a process which will give better results than presently achieved with chromia-alumina catalysts. Other objects and advantages of the present invention will be apparent from the following description.

DESCRIPTION OF THE INVENTION AND PREFERRED EMBODIMENTS

The objects of the present invention have been achieved by use of a novel catalyst containing chromium, magnesium, aluminum and oxygen. The catalysts are characterized as magnesium chromites either in admixture with aluminum oxide or containing aluminum therein and can be considered as aluminum promoted magnesium chromites. The chromites generally have a spinel structure. This can be attributed to the octahedral site preference energy of $Cr^{3+}$ which is the greatest of all cations which can form spinel-type structures. The crystal structure of the chromites will usually be a face centered cubic form.

The catalysts of the present invention are predominately chromites, that is, they contain more than 50% by weight of the chromite. Preferably the catalysts contain 75% or more chromites, i.e., 90% chromites. The chromites generally may be represented by the formula $MeCr_2O_4$ where Me as stated above is Mg, however, a portion of the magnesium can be replaced with other metals having an ionic radius approximately between about 0.5 and 1.1A, preferably between about 0.6 and 1.0A. In the case of such mixed chromites, Mg will be the predominant Me ion, comprising at least 50 atomic % of the Me ions present. In addition to Mg the Me may be one or more of the divalent ions of Ca, Sr, Ba, Fe, Mn, Co, Ni, Cu, Zn, or Cd.

The aluminum component of the catalyst may also be present as a constituent of the chromite, however, it is not necessary that the aluminum be a portion of the chromite and may be present in addition to the metal chromite in the form of aluminum oxide. The aluminum can be incorporated into the chromite by backing out a portion of the chromium. Aluminum can be substituted for up to less than 50% of the chromium atoms of the chromite. Such chromites have the formula $MeAl_xCr_{2-x}O_4$ where Me has the designation previously given and x is a number of from more than 0 up to less than 1.

The magnesium chromites of the present invention exhibit a certain type of X-ray diffraction pattern. The peaks observed in the X-ray diffraction pattern may not have sharp peaks such as those found, e.g., in highly crystalline material of the same chemical composition, but can and do frequently exhibit relatively broad reflection peaks. The degree of sharpness of the reflection peak may be measured by the reflection peak band width at half height (W/h/2). In other words, the width of the reflection peak as measured at one-half of the distance to the top of the peak is the "band width at half height". The band width at half height is measured in units of °2 theta. Techniques for measuring the band widths are discussed, e.g., in Chapter 9 of Klug and Alexander, X-ray Diffraction Procedures, John Wiley and Son, N.Y., 1954. The observed band widths at half height of the preferred compositions of this invention are at least 0.12 °2 theta and normally will be at least 0.16 °2 theta.* The particular reflection peak used to measure the band width at one-half height is the reflection peak having Miller (hkl) indices of 111. (See, e.g., Chapter of Klug and Alexander, ibid). This description is not to be taken as a limitation of the invention in regard to the relationship between composition activity and band width. 6 *The powder diffraction patterns may be made, e.g., with a Norelco constant potential diffraction unit type No. 12215/0, equipped with a wide range goniometer type No. 42273/0, copper tube type No. 32147, proportional counter type No. 57250/1; all coupled to the Norelco circuit panel type No. 12206/53. The copper K alpha radiation is supplied by operating the tube at a constant potential of 40 kilovolts and a current of 35 milliamperes. A nickel filter is used to remove K beta radiation. The detector voltage is 1660 volts and the pulse height analyzer is set to accept pulses with amplitudes between 10 and 30 volts only. Slits used are divergence 1°, receiving 0.006 inches and scatter 1°. Strip chart recordings for identification are made with a scanning speed of 1° per minute, time constant of 1 second and a full scale at 10³ counts per second. No correction is made for Kα doublet or instrumental broadening of the band widths.

Suitable catalyst according to this invention are magnesium chromite having X-ray diffraction peaks with the d-spacings 480-482, 294-296, 250-252, 240-242, 207-209, 190-192, 169-171, 159-161, 146-148, 140-142, and the most intense peaks being between 250-252.

Chromite formation can be accomplished by reacting an active compound of chromium with an active compound of magnesium and the other designated metals. By active compound is meat a compound which is reactive under the conditions rto form the chromite. Starting compounds of chromium, magnesium or the other metals may be such as the nitrates, hydroxides, hydrates, oxalates, carbonates, acetates, formates, halides, oxides, etc.

The catalyst may contain an excess of chromium over the stoichiometric amount, with is 2 atoms of chromium per atom of Me ($MeCr_2C_4$). There may be from 10 to 200 percent excess of the chromium. Similarly the Me portion of the chromite may be present in more than a stoichiometric amount.

The magnesium chromite can be prepared by precipitation, dry or wet milling or mixing, by precipitation of one of the ingredients in the presence of the other, coprecipitation and impregnation of one or more of the solid ingredients with aqueous or non-aqueous solutions of salts of the ingredients.

One particularly useful method of preparing the magnesium chromites has been by coprecipitation from an aqueous solution. Soluble metal salts of chromium, magnesium and any other metal component as described above are dissolved in water and an insoluble precipitate formed by the use of a precipitating agent.

Soluble metal salts are known for essentially all metals. In specific regard to the metal components of the present invention the following soluble metal compounds are illustrative: chromium (III) nitrate, magnesium chloride, calcium sulfate, strontum tetrasulfide tetrahydrate, barium trisulfide, iron (II) nitrate, manganese (II) dithionate, cobalt (II) acetate, nickel nitrate, copper nitrate, zinc sulfate, cadimum sulfate and aluminum sulfate. The precipitating agent in any compound which when reacted with the metal ion portion of the catalyst forms an insoluble compound which can be converted to the chromite. The alkali and alkaline earth hydroxides such as NaOH, KOH, CaOH, as well as ammonium hydroxide cause the precipitation of the metal hydroxides which are converted on heating to the chromites. After the precipitate is washed and dried it is calcined to form the chromite.

The formation of the chromite is obtained by heating the precipitates or other intimate mixture of chromite precursors at an elevated temperature, e.g., 400°-1100° C (generally no greater than 1300° C), in a controlled atmosphere, i.e., air, nitrogen, helium, a reducing atmosphere such as hydrogen carbon monoxide or the like, for a sufficient time, i.e., usually 5 minutes to 4 hours. A calcination temperature of 550°-800° C has been found particularly useful and temperatures in the range of 600°-750° C. have been found to produce excellent catalysts. Catalysts prepared at 900°-1100° C have also been found to be highly desirable.

The aluminum component of the catalyst as stated above can be added prior to and/or after the calcination and formation of the chromite. The aluminum component is conveniently added to the chromite as a soluble salt in a slurry with the chromite after which it is dried then decomposed by heating to aluminum oxide. Alternatively insoluble aluminum oxide can be added to the magnesium chromite, preferably in a highly divided state. Yet another desirable way to place the aluminum in the catalyst is by coprecipitation of aluminum hydroxide with the Me hydroxide and chromium hydroxide.

The aluminum will be present in the catalyst in all forms in an atomic ratio of Al:Cr of 0.0004 to 1.2:1. For example, in terms of a soluble aluminum compound such as aluminum sulfate, added to the magnesium chromite this would represent from about 0.1 to 75 weight percent $Al_2(SO_4)_3$ $16H_2O$ based on the total weight of the catalyst. A more preferred range of Al:Cr atom ratio is .04 to 0.8:1. Generally the higher weight percentages of aluminum compound, i.e., 50 weight percent or more, are applied to the magnesium chromites having high surface areas, e.g., 50 m² per gram or more.

The active catalysts can be pelleted or applied to a suitable support, such as alumina, silica gel, silica-alumina, firebrick, kieselguhr, quartz and the like. The catalyst is the active surface available for contact with the gaseous reactants.

The catalysts of this invention can be applied to the dehydrogenation of a wide variety of organic compounds. Such compounds normally will contain from 2 to 20 carbon atoms, at least one

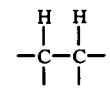

grouping, having a boiling point below about 350° C., and may contain other elements, in addition to carbon and hydrogen such as oxygen, halogens, nitrogen and sulfur. Preferred are compounds having 2 to 12 carbon atoms, and especially preferred are compounds of 3 to 5 carbon atoms.

Representative materials which are dehydrogenated by the novel process of this invention include n-butane, ethyl toluene, alkyl chlorobenzenes, ethyl naphthalene, isobutyronitrile, propyl chloride, isobutyl chloride, ethyl fluoride, ethyl bromide, n-pentyl iodide, ethyl dichloride, 1,3-dichlorobutane, 1,4-dichlorobutane, the chlorofluoroethanes, methyl pentane, methylethyl ketone, diethyl ketone, n-butyl alcohol, methyl propionate, and the like.

Among the types of organic compounds which may be dehydrogenated by means of the process of this invention are nitriles, amines, alkyl halides, ethers, esters, aldehydes, ketones, alcohols, acids, alkyl aromatic compounds, alkyl heterocyclic compounds, cycloalkanes, alkanes, alkenes and the like.

Suitable dehydrogenation reactions are the following: acyclic compounds having 4 to 5 non-quaternary contiguous carbon atoms to the corresponding olefins, diolefins or acetylenes having the same number of carbon atoms; aliphatic hydrocarbons having 6 to 16 carbon atoms and at least one quaternary carbon atom to aromatic compounds, such as 2,4,4-trimethylpentene-1 to a mixture of xylenes; acyclic compounds having 6 to 16 carbon atoms and no quaternary carbon atoms to aromatic compounds such as n-hexanes to benzene; cycloparaffins and cycloolefins having 5 to 8 carbon atoms to the corresponding olefin, diolefin or aromatic compound, e.g. cyclohexane to cyclohexene or cyclohexadiene or benzene; aromatic compounds having 8 to 12 carbon atoms including one or two alkyl side chains of 2 to 3 carbon atoms to the corresponding aromatic with unsaturated side chain such as ethyl benzene to styrene.

Illustration of dehydrogenations include butane to butenes and butadiene propionitrile to acrylonitrile; propionaldehyde to acrolein; ethyl chloride to vinyl chloride; methyl isobutyrate to methyl methacylate; 2 or 3-chlorobutene-1 or 2,3-dichlorobutane to chloroprene; ethyl pyridine to vinyl pyridine; ethylbenzene to styrene; isopropylbenzene to α-methyl styrene; ethylchlorohexane to styrene; cyclohexane to benzene; ethane to ethylene to acetylene; propane to propylene or methyl acetylene, allene, or benzene; isobutane to isobutylene; n-butane to butene and butadiene-1,3; n-butene to butadiene-1,3 and vinyl acetylene; methyl butene to isoprene; cyclopentane to cyclopentene and cyclopentadiene-1,3; n-octane to ethyl benzene and ortho-xylene; monomethylheptanes to xylenes; ethyl acetate to vinyl acetate; 2,4,4-trimethylpentane to xylenes; and the like.

The preferred compounds to be dehydrogenated are hydrocarbons with a particularly preferred class being acyclic non-quaternary hydrocarbons having 3 to 5 carbon atoms or ethyl benzene and the preferred products are propene, n-butene-1 or 2, butadiene-1,3, vinyl acetylene, 2-methyl-1-butene, 3-methyl-1-butene, 3-methyl-2-butene isoprene, styrene or mixtures thereof. Especially preferred as feed are n-butene-1 or 2 and the methyl butenes and mixtures thereof such as hydrocarbon mixtures containing these compounds in at least 50 mol percent.

The dehydrogenation reaction may be carried out at atmospheric pressure, superatmospheric pressure or at sub-atmospheric pressure. The total pressure of the system will normally be about atmospheric pressure or sub-atmospheric pressure. Generally the total pressure will be between about 1 p.s.i.a. and about 75 p.s.i.a. Preferably the total pressure will be less than about 50 p.s.i.a.

The temperature of the dehydrogenation reaction will generally be in a range of about 350° to 700° C with excellemt results being obtained in the range of 400° to 650° C. The gaseous reactants can be conducted through the reaction chamber at a fairly wide range of flow rates. The optimum flow rates will be dependent upon such variables at the temperature of reaction, pressure, particle size of the catalyst, and so forth. Desirable flow rates may be established by one skilled in the art. Generally the flow rates will be within the range of about 0.10 to 10 liquid volumes of the organic compound to be dehydrogenated per volume of dehydrogenation zone containing catalyst per hour (referred to as LHSV). Usually the LHSV will be between 0.15 and about 5. For calculation, the volume of a fixed bed dehydrogenation zone containing catalyst is that original void volume of reactor space containing catalyst.

The dehydrogenation is carried out in a series of cycles which comprise dehydrogenation of a suitable feed over the catalysts of the invention under the conditions as defined for a period of time, usually about 6 to 12 minutes followed by a regeneration cycle during which the coke deposited from the dehydrogenation is burnt off. The regeneration can no longer be shorter than the dehydrogenation cycle as needed to remove the coke, usually about 6 to 12 minutes will be sufficient. The coke is removed by passing oxygen at a temperature of 550° to 650° C. over the catalyst. A convenient source of oxygen is air, however, pure oxygen or a mixture of oxygen with inert gases, such as nitrogen, either in the same or different proportions as air, can be used.

The following Examples which are submitted to demonstrate the operation of the invention are divided into two sections relative to the reactor. In the first Example section the process was carried out at atmospheric pressure, i.e., about 15 p.s.i.a. In the second section the reactions were carried out under vacuum. The absolute number of the results vary as a result of the different conditions, however, the trends, results and relative differences in catalysts types are comparable. The presence of the chromite structure was established for the catalysts by X-ray analysis as described previously. In the Examples percents are by weight except that results are given as mole percents. Analysis of the products was by gas-liquid chromatography.

EXAMPLE 1

The coprecipitated catalysts were prepared by the same method. In each instance $CrCl_3.6H_2O$ and $MgCr_2.6H_2O$ (in some cases $AlCl_3.6H_2O$) were dissolved in demineralized water with about 1.4% dextran* to produce an atom ratio of Mg/Cr of ½ unless specified otherwise. This solution was then added to concentrated $NH_4OH$, the precipitate filtered, washed and dried at 160° C. then passed through an 80 mesh screen and calcined for 1 hour at the indicated temperature in air (unless specified otherwise) and run through a hammer mill. The soluble salts, e.g., $Al_2(SO_4)_3.16H_{20}$, were added by dissolving the salt in water, forming a slurry with the chromite (or in some cases the comparative commercial catalyst) and heating the slurry to dryness in a mechanical tumbler to obtain even distribution of the soluble salts. The same procedure was used to deposit the actives on a support. 6 *(Dextran is a polysaccharide of 200,000 – 300,000 M. wt. and improves the processability of the precipitate.)

Isothermal Atmospheric Reactor (EXAMPLES 2–23)

The reactor was a 20 × ¾ inch Vycor tube equipped with a heating mantle and appropriate equipment. A 40 cc bed of catalyst was placed in the reactor and reactant feed (or regenerative air) added at the bottom of the reactor with product coming off overhead. The catalyst was heated to the reaction temperature in a nitrogen atmosphere. The process was carried out automatically with a make cycle (dehydrogenation) of 9 minutes and 9 minutes oxygen regeneration and repeat of the cycle. This gave a total cycle time of 18 minutes. When desired, the partial pressure of the n-butane during the reaction cycle was reduced below atmopsheric by dilution with nitrogen. The total effluent from either or both cycles was collected in an inflatable collecting device and analyzed by gas chromatography. Alternately, the effluent from the regeneration cycle was passed through a callibrated infrared analyzer to determine the amount of $CO_2$ produced during regeneration (coke burn-off). By either method of analysis the amount of coke deposited on a catalyst during the reaction cycle was determined and could be taken into account when calculating the overall activity and selectivity of a catalyst. The temperatures were controlled by a thermoelectric temperature controller and recorded on a Leeds and Northrup 24-point recorder.

EXAMPLES 2–11

These Examples demonstrate the improvement accomplished according to the present invention. The feed was 99 mole % n-butane. The conditions and results are set out in Table I.

TABLE I

Conditions: LHSV = 1.0 $T_m$ = ~ 600° C. Reaction Cycle = 9 minutes reaction/ 9 minutes regeneration

| Example | Catalyst | Partial Pressure n-$C_4$ (Atm.)[3] | Total Hrs. on Stream | Results Mole % | | | |
|---|---|---|---|---|---|---|---|
| | | | | S | | Y | |
| | | | | C | Bu | Bd | Bu | Bd |
| 2 | Harshaw[7] CrO2 11,5/32" diameter pellets | 1.0 | 24 | 69 | 65 | 5 | 45 | 7 |
| | | 0.33 | 26 | 67 | 69 | 10 | 46 | 7 |
| 3 | Houdry[8] C, 1/8" extrusions | 1.0 | 24 | 77 | 64 | 8 | 49 | 7 |
| | | 0.33 | 26 | 79 | 65 | 16 | 50.5 | 13 |
| 4 | 5/32" pellets of $MgCr_2O_4$ | 1.0 | 24 | 44 | 54 | 8.5 | 24 | 4 |
| | | 0.33 | 26 | 38 | 48 | 16 | 18 | 6 |
| 5 | 5/32" pellets of $MgCr_2O_4$ + 26 wt % $Al_2(SO_4)_3 \cdot 18H_2O$ | 1.0 | 24 | 57 | 67 | 9 | 38 | 5 |
| | | 0.33 | 26 | 56 | 66 | 15 | 37 | 8 |
| 6 | 5/32" pellets, $MgCr_2O_4$ 6 + 20% $Al_2(SO_4)_3 \cdot 18H_2O$ | 1.0 | 24 | 58 | 66 | 8 | 38 | 5 |
| | | 0.33 | 26 | 55 | 63 | 15 | 35 | 8 |
| 7 | $MgCr_2O_4$, [1,2,4] | 1.0 | 24 | 51 | 64 | 8 | 33 | 4 |
| | | 0.33 | 26 | 46 | 61 | 15 | 28 | 7 |
| 8 | $MgCr_2O_4$[1,2,4] + 0.012 mols $Al_2(SO_4)_3 \cdot 18H_2O$ | 1.0 | 24 | 59 | 66 | 8 | 39 | 5 |
| | | 0.33 | 26 | 57 | 63 | 14 | 36 | 8 |
| | | 0.33 | 26 | 57 | 63 | 14 | 36 | 8 |
| 9 | $MgCr_2O_4$[1,2,4] + 0.024 moles $Al_2(SO_4)_3 \cdot 18H_2O$ | 1.0 | 24 | 64 | 69 | 8 | 47 | 5 |
| | | 0.33 | 26 | 66 | 68 | 14 | 44 | 9 |
| 10 | $MgCr_2O_4$[1,2,4] + 0.037 moles $Al_2(SO_4)_3 \cdot 18H_2O$ | 1.0 | 24 | 66 | 68 | 8 | 45 | 5 |
| | | 0.33 | 26 | 68 | 67 | 15 | 46 | 10 |
| 11 | $MgCr_2O_4$[1,2,4] + 0.012 moles $H_2SO_4$ | 1.0 | 24 | 52 | 62 | 8 | 32 | 4 |

Notes:
[1] Coprecipitate of Cr/Mg 2/1 calcined at 600° C for 1 hour in air
[2] Catalysts are 6-8 mesh particles of ~ 55% actives deposited on 7-9 mesh, HCl leached AMC alumina
[3] pp of n-$C_4$ = 1.0 atm = pure hcbn feed; pp of n-$C_4$ = 0.33 atm. = hcbn + $N_2$ diluent
[4] 66.7 gms. of $MgCr_2O_4$
[5] C = conversion, S = selectivity, Y = yield, Bu = butenes, Bd = butadiene.
[6] Uncalcined coprecipitate Cr/Mg = 2/1 + 20% $Al_2(SO_4)_3 \cdot 18H_2O$ then calcined at 600° C for 2 hours in air
[7] The Harshaw Chemical Co., Cleveland, Ohio
[8] Houdry Products and Chemical Co., Philadelphia, Pa.

Examples 1 and 2 are two commercial catalyst employed in cyclic processes for dehydrogenation of butane. Examples 4 and 5 are $MgCrO_4$ which was pelleted and 6 through 10 are 55% actives deposited on a fused alumina support. Example 11 was to determine if the sulfate was of any benefit. By comparison of Examples 11 and 7 it can be seen that the sulfate is of no benefit.

EXAMPLES 12 AND 13

These Examples show the improvement obtained with aluminum salts other than the sulfate using 99 mole % butane as the feed. The conditions and results are set out in TABLE II.

TABLE II

Conditions: LHSV = 1.0 $T_m$ = ~ 600° C., Reaction cycle = 9 minutes reaction/ 9 minutes regeneration

| Example | Catalyst[1] | Partial Pressure of n-$C_4$ (Atm.)[2] | Results Mole % | | | |
|---|---|---|---|---|---|---|
| | | | | S | | Y |
| | | | C | Bu | Bd | Bu | Bd |
| 12 | 42.5 gms. $MgCr_2O_4$[3] + 0.044 moles of $Al(CH_3COCHCOCH_3)_3$ | 1.0 | 58 | 67 | 9 | 39 | 6 |
| | | 0.33 | 52 | 61 | 17 | 32 | 9 |
| 13 | 42.5 gms. of $MgCr_2O_4$[3] + 0.044 moles of $Al(NO_3)_3 \cdot 9H_2O$ | 1.0 | 62 | 70 | 8 | 43 | 5 |
| | | 0.33 | 61 | 68 | 15 | 41 | 9 |

[1] Supported on 7-9 mesh AMC alumina
[2] pp of n-$C_4$ = 1.0 atm. = pure hcbn feed; pp of n-$C_4$ = 0.33 atm. = hcbn + $N_2$
[3] coprecipitated, calcined at 600° C. for 2 hours in air and run through a hammer mill.

EXAMPLES 14–19

These Examples demonstrate the effect of the calcination temperature of the $MgCr_2O_4$ on the process results. Table III shows the conditions and results.

TABLE III

Conditions: LHSV = 1.0 $T_m$ = ~ 600° C, Reaction Cycle = 9 minutes reaction/ 9 minutes regeneration approx. 24 hours on stream for each run Feed n-butane (99 mole %)

| Example | Catalyst[1] | Partial Pressure of n-$C_4$ (Atm.)[2] | Results | | | |
|---|---|---|---|---|---|---|
| | | | | S | | Y |
| | | | C | Bu | Bd | Bu | Bd |
| 14 | Coprec. of Cr/Mg = 2/1 calcined to 550° C; 42.5 gms. of calcined product + 0.022 moles of $Al_2(SO_4)_3 \cdot 18H_2O$ | 1.0 | 67 | 68 | 10 | 45 | 7 |
| | | 0.33 | 66 | 65 | 17 | 43 | 11 |
| 15 | Coprec. of Cr/Mg = 2/1 calcined to 600° C; 42.5 gms. of calcined product + 0.022 moles of $Al_2(SO_4)_3 \cdot 18H_2O$ | 1.0 | 67 | 68 | 10 | 45 | 7 |
| | | 0.33 | 68 | 65 | 18 | 43 | 12 |
| 16 | Coprec. of Cr/Mg = 2/1 calcined to 650° C; 42.5 gms of calcined product + 0.022 moles of $Al_2(SO_4)_3 \cdot 18H_2O$ | 1.0 | 68 | 70 | 9 | 48 | 6 |
| | | 0.33 | 67.5 | 70 | 15 | 47 | 10 |
| 17 | Coprec. of Cr/Mg = 2/1 calcined to 700° C; 42.5 gms. of calcined product + 0.022 moles of $Al_2(SO_4)_3 \cdot 18H_2O$ | 1.0 | 59 | 76 | 10 | 45 | 6 |
| | | 0.33 | 55 | 74 | 17.5 | 41 | 10 |
| 18 | Coprec. of Cr/Mg = 2/1 calcined to 750° C; 42.5 gms. of calcined product + 0.022 moles of $Al_2(SO_4)_3 \cdot 18H_2O$ | 1.0 | 60 | 74 | 9 | 45 | 5 |
| | | 0.33 | 58 | 76 | 16 | 44 | 9 |
| 19 | Coprec. of Cr/Mg = 2/1 calcined to 800° C; 42.5 gms. of calcined product + 0.022 moles of $Al_2(SO_4)_3 \cdot 18H_2O$ | 1.0 | 47 | 77 | 11 | 37 | 5 |
| | | 0.33 | 42 | 72.5 | 20 | 31 | 8 |

Notes:
[1] Supported on 7-9 mesh AMC alumina
[2] pp of n-$C_4$ = 1.0 atm. = pure hcbn feed; pp of n-$C_4$ = 0.033 atm. = hcbn + $N_2$.

The noticeable trends with increasing calcination temperature are the decrease in conversion but substantial increase in selectivities.

EXAMPLES 20 AND 21

These examples are presented to show the combination of Al in a chromite of the formula $MgAl_xCr_{2-x}O_4$. Table IV sets forth the concition and results.

TABLE IV

Conditions: LHSV = 1.0, $T_m = \sim 600°$ C,
Reaction Cycle = 9 minutes reaction/
9 minutes regeneration.
Feed: 99 mole % butane
Hours on stream ≅ 24

| Example | x in $MgAl_xCr_{2-x}O_4$[1] | Partial Pressure n-$C_4$ (Atm.)[2] | Results | | | |
|---|---|---|---|---|---|---|
| | | | C | S | | Y |
| | | | | Bu | Bd | Bu  Bd |
| 20 | 0.0 | 1.0 | 51 | 74 | 7 | 37.5  3 |
| | 0.1 | 1.0 | 63 | 67 | 8 | 42  5 |
| | 0.2 | 1.0 | 64 | 65 | 9 | 42  6 |
| | 0.3 | 1.0 | 66 | 68 | 7 | 45  5 |
| | 0.4 | 1.0 | 67 | 69 | 6.5 | 47  4 |
| | 0.5 | 1.0 | 68 | 69 | 8 | 47  5.5 |
| 21 | 0.0 | 0.33 | 42 | 64 | 15 | 27  6 |
| | 0.1 | 0.33 | 62 | 65 | 15 | 40  9 |
| | 0.2 | 0.33 | 62 | 64 | 16 | 40  10 |
| | 0.3 | 0.33 | 69 | 69 | 12 | 48  8.5 |
| | 0.4 | 0.33 | 67 | 66 | 14 | 44  9 |

Notes:
[1] 6–8 mesh particles of 50 wt. % actives deposited on 7–9 mesh, HCl leached AMC alumina support.
[2] pp of n-$C_4$ ≅ 1.0 atm. = pure hcbn feed; pp of n-$C_4$ = 0.33 atm. = hcbn + $N_2$ diluent.

The catalysts were prepared in the same manner as in Example 1 with $Al_2(SO_4)_3$ being added in the appropriate amount. The coprecipitated catalysts were calcined at 600° C for 2 hours in air and hammer milled.

No substantial advantage was obtained from adding an additional 20% $Al_2(SO_4)_3.18H_2O$ to the calcined $MgAl_xCr_{2-x}O_4$ catalyst.

EXAMPLE 22

The catalyst in this case was prepared by depositing a slurry of 4.4% $Al_2O_3$ and 95.6% $MgCr_2O$ (calcined coprecipitated at 600° C. for 2 hours in air) on to HCl leached alumina and drying the catalyst. 4.4% $Al_2O_3$ corresponds to 20% $Al_2(SO_4)_3.16H_2O$. The $Al_2O_3$ was approximately 90% gamma alumina (Alon fumed alumina). The dehydrogenation was carried out at 1 atmosphere using pure n-butane at LHSV of 1 at 600° C. for about 24 hours using the 9/9 minute cycle. The results were

| | | Mole % | | |
|---|---|---|---|---|
| C | $S_{Bu}$ | $S_{Bd}$ | $Y_{Bu}$ | $Y_{Bd}$ |
| 60 | 74 | 12 | 44 | 7 |

EXAMPLE 23

This series of runs was made to demonstrate the catalyst with an excess of either Mg or Cr over the stoichiometric amount. The variation was obtained by using the proportion of soluble salts to give the Mg:Cr atom ratios shown in Table V. The improvement for each ratio with added Al is also shown in Table V along with the conditions.

TABLE V

Conditions:
LHSV = 1.0, atmospheric pressure temperature ≅ 600° C,
reaction cycle 9 minutes reaction/9 minutes regeneration.
Feed: 99 mole % n-butane

| | Results | | | | | | | |
|---|---|---|---|---|---|---|---|---|
| | Without Al Mole % | | | | 20%:$Al_2(SO_4)_3.16H_2O$ Mole % | | | |
| x in $Mg_{1.0}Cr_xO_4$ | C | S | | Y | | C | S | | Y | |
| | | Bu | Bd | Bu | Bd | | Bu | Bd | Bu | Bd |
| 1.7 | 36 | 65 + 12 | | 24 + 4 | | 62 | 68 + 13 | | 42 + 8 | |
| 1.8 | 44 | 69 + 10 | | 30 + 5 | | 67 | 63 + 15 | | 42 + 10 | |
| 1.9 | 42 | 68 + 11 | | 29 + 5 | | 67 | 65 + 11 | | 44 + 8 | |
| 2.0 | 46 | 67 + 10.5 | | 31 + 5 | | 64 | 65 + 12 | | 42 + 8 | |
| 2.1 | 41.6 | 64 + 12 | | 27 + 5 | | 69 | 68 + 12 | | 47 + 8 | |
| 2.2 | 42 | 61 + 12 | | 26 + 5 | | 65 | 66 + 11 | | 43 + 7.5 | |
| 2.3 | 41 | 57 + 13 | | 24 + 5 | | 64 | 68 + 12.5 | | 44 + 8 | |

Isothermal Vacuum Reactor

(EXAMPLES 24–47)

The reactor was an alonized 316 SS tube, 24 inches long and 1 inch in diameter equipped with a heating mantel and thermoelectric temperature controller. A 160 cc bed of catalyst (112 cc of catalyst mixed with 48 cc of fused alumina balls) was used for each run. The reactant feed was passed down through the catalyst bed and the products removed at the bottom. The catalyst was heated to reaction temperature in a nitrogen atmosphere. The process was carried out in cycles of 9 minutes of reaction, 1 minute of nitrogen purge, 9 minutes of regeneration, folowed by reaction, etc. A vacuum of 22 inches of Hg was maintained during the reaction cycle and atmosphere pressure used during nitrogen purge and regeneration cycle. Substantially the same analytical procedures were followed for the product gases as in the atmospheric process.

EXAMPLES 24–27

These four examples demonstrate the invention having the aluminum compound added after (Ex. 25) and before (Ex. 26) calcination. Example 24 is the control. Table VI contains the conditions and results of the run.

TABLE VI

Conditions: LHSV = 1.25. $T_m = \sim 550°$ C (1022° F), Pressure = 22" Hg vacuum

| 9 min. reaction | 1 min. $N_2$ purge | 9 min. regeneraton |
|---|---|---|
| Reaction Cycle = 590 cc/min. of n-$C_4$ Feed: 99 mole % n-butane | | 1500 cc/min. of artificial air = 300 cc/min. $O_2$ + 1200 cc/min. $N_2$, |

| Example | Catalyst | Total Hrs. on Stream | Results, Mole % | | | |
|---|---|---|---|---|---|---|
| | | | C | S | | Y | |
| | | | | Bu | Bd | Bu | Bd |
| 24 | 5/32" dia. $MgCr_2O_4$ (coprec. of Cr/Mg = 2/1 calcined to 600° C) | 90.5 | 22.4 | 70.8 + 10.6 | | 15.8 + 2.4 | |
| | | 138.5 | 21.1 | 68.4 + 11.2 | | 14.4 + 2.4 | |
| | | 206.0 | 19.8 | 67.1 + 12.0 | | 13.3 + 2.4 | |
| 25 | 5/32" dia. pellets of $MgCr_2O_4$ (coprec. of Cr/Mg = 2/1 calcined to 600° C)+ 26 wt. % $Al_2(SO_4)_3.18H_2O$[2] | 21.5 | 50.2 | 77.0 + 6.9 | | 38.6 + 3.5 | |
| | | 44.5 | 61.0 | 72.1 + 7.9 | | 44.0 + 4.8 | |
| | | 120.5 | 60.2 | 73.6 + 8.0 | | 44.3 + 4.8 | |
| | | 334.5 | 59.7 | 73.7 + 6.0 | | 44.0 + 3.6 | |
| | | 501.5 | 58.5 | 76.7 + 5.8 | | 44.8 + 3.4 | |
| 26 | non-calcined coprec. | 115.0 | 44.5 | 74.3 + 10.5 | | 33.1 + 4.7 | |

TABLE VI-continued

Conditions: LHSV = 1.25. $T_m = \sim 550°$ C (1022° F), Pressure = 22" Hg vacuum

| | | | | | |
|---|---|---|---|---|---|
| | of Cr/Mg = 2/1 + | 161.0 | 44.9 | 76.0 + 10.3 | 34.1 + 4.6 |
| | appropriate amount of | 234.0 | 40.4 | 76.5 + 10.1 | 30.9 + 4.1 |
| | $Al_2(SO_4)_3 \cdot 18H_2O$ and | 334.0 | 39.3 | 77.6 + 11.1 | 30.5 + 4.4 |
| | the mixture calcined to | | | | |
| | 600° C and formed into | | | | |
| | 5/32" dia. $MgCr_2O_4$ | | | | |
| | pellets | | | | |
| 27 | 5/32" dia. pellets | 95.0[1] | 67.8 | 63.7 + 7.1 | 43.2 + 4.8 |
| | $Mg/Cr_2O_4$ coprec of | 190.5[1] | 64.5 | 66.6 + 8.4 | 42.9 + 5.4 |
| | Cr/Mg = 2/1 calcined | 214.5[2] | 53.5 | 75.1 + 7.1 | 40.2 + 3.8 |
| | to 600°C + 38 wt. % | 239.0[2] | 55.4 | 75.6 + 7.2 | 41.9 + 4.0 |
| | $Al(NO_3)_3 \cdot 9H_2O$ | 334.0[2] | 56.3 | 75.1 + 7.1 | 42.3 + 4.0 |
| | | 382.5[2] | 57.1 | 74.6 + 7.4 | 42.6 + 4.2 |
| | | 526.5[2] | 55.1 | 77.2 + 8.4 | 42.9 + 4.7 |

[1]Flow of $O_2$ was increased from 300 cc/min to 345 cc/min to effect complete regeneration.
[2]$T_m = 525°$ C

EXAMPLES 28, 29 AND 30

These examples show a range of aluminum concentrations in the catalyst. Table VII shows the conditions and reslults.

TABLE VII

Conditions: LHSV = 1.25   Pressure = 22" Hg vacuum 9 min. reaction
Reaction Ccycle = 59 cc/min of n-$C_4$.
Feed: 99 mole % n-butane 1 min. $N_2$ purge 9 min. regeneration
1500 cc/min. of artifical air = 300 cc/min. $O_2$ + 1200 cc/min. $N_2$.

| Example | Catalyst | Total Hrs. on Stream | $T_m$, °C | C | S Bu | Bd | Y Bu | Bd |
|---|---|---|---|---|---|---|---|---|
| 28 | 5/32" dia. pellets of | 23.0 | 550 | 56.8 | 71.5 + | 9.2 | 40.6 + | 5.2 |
| | $MgCr_2O_4$ (coprec. of | 94.5 | 550 | 59.4 | 70.5 + | 9.3 | 41.9 + | 5.5 |
| | Cr/Mg = 2/1 cal- | 117.5 | 550 | 60.2 | 69.1 + | 9.6 | 41.6 + | 5.8 |
| | cined to 700° C) + 15 | 141.5 | 550 | 60.0 | 70.3 + | 9.8 | 42.2 + | 5.9 |
| | wt. % $Al_2(SO_4)_3 \cdot 16$ | 165.5 | 525 | 50.5 | 78.6 + | 7.9 | 39.7 + | 4.0 |
| | $H_2O$ | 189.5 | 525 | 52.1 | 79.1 + | 7.3 | 41.2 + | 3.8 |
| 29 | 5/32" dia. pellets of | 69.5 | 550 | 56.0 | 72.2 + | 9.0 | 40.5 + | 5.1 |
| | $MgCr_2O_4$ (coprec. of | 97.5 | 550 | 57.7 | 73.1 + | 8.6 | 42.2 + | 4.9 |
| | Cr/Mg = 2/1 cal- | 117.5 | 550 | 59.2 | 75.1 + | 8.8 | 44.5 + | 5.2 |
| | cined to 700° C) + 20 | 165.5 | 550 | 59.0 | 73.2 + | 8.9 | 43.1 + | 5.2 |
| | wt. % $Al_2(SO_4)_3 \cdot 16$ $H_2O$ | 238.0 | 550 | 59.4 | 73.0 + | 9.8 | 43.4 + | 5.8 |
| 30 | 5/32" dia. pellets of | 67.0 | 550 | 59.3 | 71.2 + | 11.0 | 42.2 + | 6.5 |
| | $Mg/Cr_2O_4$ (coprec. of | 90.5 | 550 | 59.7 | 71.1 + | 10.9 | 42.4 + | 6.5 |
| | Cr/Mg = 2/1 cal- | 186.0 | 550 | 60.1 | 71.8 + | 10.3 | 43.1 + | 6.2 |
| | cined to 700° C) + | 321.0 | 525 | 48.2 | 81.5 + | 7.8 | 39.3 + | 3.7 |
| | 25 wt. % $Al_2(SO_4)_3 \cdot 16H_2O$ | | | | | | | |

EXAMPLES 31–34

The effect of the calcination temperature is shown in these examples. As in the reaction run at atmospheric pressure the $MgCr_2O_4$ produced at increasing calcination temperatures provided higher selectivities with lower conversions under similar operating conditions. This can be seen in Table VIII.

TABLE VIII

Conditions: LHSV = 1.25   $T_{max} \sim 550°$ C.   Pressure = 22" Hg vacuum 9 min. reaction
590 cc/min. of n-$C_4$.
Feed: 99 mole % n-butane 1 min. $N_2$ purge 9 min. regeneration
1500 cc/min. of artifical air = 300 cc/min. $O_2$ + 1200 cc/min. $N_2$

| Example | Catalyst[1] | Total Hrs. on Stream | $T_m$ °C | C | S Bu | Bd | Y Bu | Bd |
|---|---|---|---|---|---|---|---|---|
| 31 | $MgCr_2O_4$ calcined to 600° C | 164.5 | 550 | 65.7 | 64.9 + | 11.9 | 42.6 + | 7.8 |
| | | 282.5 | 525 | 56.2 | 75.9 + | 8.3 | 42.7 + | 4.5 |
| 32 | $MgCr_2O_4$ calcined to 650° C | 164.0 | 550 | 65.3 | 69.1 + | 11.1 | 45.1 + | 7.3 |
| | | 235.0 | 525 | 53.4 | 75.3 + | 9.4 | 40.2 + | 5.0 |
| 33 | $MgCr_2O_4$ calcined to 700° C | 307.5 | 550 | 55.9 | 69.3 + | 14.1 | 38.7 + | 7.9 |
| 34 | $MgCr_2O_4$ calcined to 750° C | 503.0 | 570 | 56.2 | 68.3 + | 17.6 | 38.4 + | 9.9 |
| | | 743.5 | 550 | 51.2 | 76.7 + | 13.5 | 39.3 + | 6.9 |

Note: [1]$MgCr_2O_4$ + 25 wt. % $Al_2(SO_4)_3 \cdot 16H_2O$ formed into 5/32" pellets.

EXAMPLES 35–42

These examples are presented by way of comparison to show the total lack of effectiveness of aluminum on two commercial dehydrogenation catalysts of the chromia-alumina type. The data is presented in Table IX.

TABLE IX

Conditions: LHSV = 1.25, $T_m = \sim 550°$ C(1022° F), Pressure = 22" Hg vacuum,
Reaction Cycle - 590 cc/min. of n-C$_4$
Feed: 99 mole % n-butane
9 min. reaction
1 min. N$_2$ purge
9 min. regeneration. 1500 cc/min. of artificial air = 300 cc/min. O$_2$ + 1200 cc/min. N$_2$.

| Example | Catalyst | Total Hrs. on stream | C/S | + S/Y Bu | Bd | + Y Bu | Bd |
|---|---|---|---|---|---|---|---|
| 35 | Houdry C, 1 8" extrusion | 45.0 | 44.2 | 77.0 | + 11.5 | 34.1 | + 5.1 |
|  |  | 139.0 | 50.6 | 80.5 | + 12.9 | 40.7 | + 6.5 |
|  |  | 163.0 | 52.4 | 80.5 | + 12.4 | 42.2 | + 6.5 |
|  |  | 188.0 | 52.1 | 80.8 | + 12.1 | 42.1 | + 6.3 |
|  |  | 355.0 | 47.8 | 83.7 | + 11.8 | 40.0 | + 5.7 |
| 36 | Houdry C + 0.016 moles (6.7 wt %) Al$_2$(SO$_4$)$_3$ . 18 H$_2$O | 67.0 | 43.4 | 83.8 | + 10.4 | 35.2 | + 4.4 |
|  |  | 118.5 | 38.9 | 84.4 | + 10.1 | 32.8 | + 3.9 |
|  |  | 139.0 | 38.2 | 84.6 | + 9.8 | 32.3 | + 3.7 |
| 37 | Houdry C + 0.037 moles (14.3 wt%)Al$_2$(SO$_4$)$_3$ . 18 H$_2$O | 47.5 | 36.7 | 81.7 | + 10.5 | 30.0 | + 3.9 |
|  |  | 96.5 | 34.7 | 81.2 | + 11.7 | 28.1 | + 4.1 |
|  |  | 171.0 | 31.4 | 83.0 | + 11.1 | 26.1 | + 3.5 |
| 38 | Houdry C + 0.047 moles (17.6 wt%)Al$_2$(SO$_4$)$_3$ . 18H$_2$O | 22.0 | 34.5 | 80.9 | + 9.3 | 27.9 | + 3.2 |
|  |  | 68.5 | 32.4 | 81.2 | + 11.3 | 26.3 | + 3.7 |
|  |  | 188.5 | 28.8 | 81.6 | + 11.7 | 23.5 | + 3.4 |
| 39 | Harshaw CrO211T,5/32" dia. pellets | 66.5 | 45.5 | 78.7 | + 11.1 | 35.8 | + 5.1 |
|  |  | 118.5 | 52.6 | 78.4 | + 10.9 | 41.2 | + 5.8 |
|  |  | 142.5 | 52.0 | 78.2 | + 11.1 | 40.6 | + 5.8 |
|  |  | 310.5 | 51.0 | 79.6 | + 11.7 | 40.6 | + 6.0 |
| 40 | Harshaw CrO211 + 0.016 moles (6.7 wt. %) Al$_2$(SO$_4$)$_3$ . 18 H$_2$O | 47.5 | 33.9 | 83.7 | + 9.2 | 28.4 | + 3.1 |
|  |  | 96.5 | 33.1 | 82.7 | + 9.4 | 27.3 | + 3.1 |
|  |  | 171.5 | 27.9 | 83.4 | + 9.8 | 23.3 | + 2.7 |
| 41 | Harshaw CrO211 + 0.026 moles (10.7 wt.%)Al$_2$(SO$_4$)$_3$ . 18 H$_2$O | 68.5 | 30.0 | 82.5 | + 9.5 | 24.7 | + 2.9 |
|  |  | 188.5 | 28.8 | 80.2 | + 11.8 | 23.1 | + 3.4 |
| 42 | Harshaw CrO211 + 0.037 moles (14.3 wt%)Al$_2$(SO$_4$)$_3$ . 18 H$_2$O | 18.0 | 21.9 | 77.7 | + 9.2 | 17.0 | + 2.0 |
|  |  | 143.0 | 24.1 | 81.0 | + 10.7 | 19.5 | + 2.6 |
|  |  | 166.0 | 24.2 | 84.6 | + 7.5 | 20.5 | + 1.8 |

EXAMPLES 43-47

These examples show the use of the catalyst of the invention and a commercial dehydrogenation catalyst in the dehydrogenation of isopentane. The conditions and results are in Table X.

TABLE X

Conditions: 6" Hg absolute
Feed : 97.6 mole % isopentane

| Example | Catalyst | LHSV | $T_{min}$-$T_{max}$ ° F Dehydrogenation | Percent Feed to Coke | C$^{(1)}$ | Selectivities mole % to | | | | |
|---|---|---|---|---|---|---|---|---|---|---|
|  |  |  |  |  |  | Isoamylenes | Iso-prene | Penta-dienes | C$_4^r$ s$^{(2)}$ | C$_5^r$ s$^{(3)}$ |
| 43 | MgCr$_2$O$_4^{(4)}$ calcined to 750° C. | 1.0 | 1070-1100 | 5.5 | 52.1 | 53.3 | 24.9 | 5.7 | 4.0 | 3.2 |
| 44 | CrO211$^{(5)}$ | 1.0 | 1075-1095 | 0.6 | 40.8 | 53.1 | 19.1 | 6.6 | 5.1 | 5.5 |
| 45 | MgCr$_2$O$_4^{(4)}$ calcined to 750° C. | 2.4 | 1000-1040 | 1.0 | 30.3 | 69.0 | 21.3 | 3.7 | 1.7 | 4.7 |
| 46 | MgCr$_2$O$_4^{(4)}$ calcined to 750° C. | 2.4 | 1070-1130 | 2.4 | 38.4 | 61.1 | 26.8 | 4.8 | 2.6 | 2.4 |
| 47 | CrO211$^{(5)}$ | 2.4 | 1075-1095 | 0.5 | 26.8 | 57.5 | 15.6 | 4.8 | 5.5 | 7.4 |

$^{(1)}$Coke free
$^{(2)}$All species
$^{(3)}$Pentene-1, n-pentane, pentene-2-cis and trans
$^{(4)}$MgCr$_2$O$_4$ + 25 wt. % Al$_2$(SO$_4$)$_3$ . 16H$_2$O formed into 5/32" pellets
$^{(5)}$The Harshaw Chemical Co., Cleveland, Ohio

The invention claimed is:

1. In the cyclic process for the non-oxidative dehydrogenation of alkyl aromatic hydrocarbon compounds to produce corresponding aromatic compounds with unsaturated side chains comprising contacting alkyl aromatic hydrocarbon compounds having 8 to 12 carbon atoms including one or two alkyl chains of 2 to 3 carbon atoms with the active surface of a catalyst to remove hydrogen from said organic compound and producing a compound having a higher degree of unsaturation than said organic compound, terminating said dehydrogenation and regenerating said catalyst by contacting said catalyst with molecular oxygen wherein the improvement comprises employing a dehydrogenation catalyst consisting essentially of magnesium chromite of the formula MeAl$_x$Cr$_{2-x}$O$_4$, having spinel structure, wherein Me is Mg or Mg and one or more of the divalent ions of Ca, Sr, Ba, Fe, Mn, Co, Ni, Cu, Zn or Cd, provided that Mg comprises at least 50 atomic percent of said Me ions and x is a number of from more than 0 up to less than 1, Me and Al being incorporated into the spinel structure, and a promoting amount of aluminum oxide intimately admixed with said magnesium chromite of the structure MeAl$_x$Cr$_{2-x}$O$_4$, said active surface in contact with the gaseous reactants having aluminum in all forms, and chromium in an Al:Cr atomic ratio of from 0.0004 to 1.2:1.

2. The process according to claim 1 wherein the aromatic compound is ethyl benzene.

3. The process according to claim 1 wherein the atomic ratio of Al:Cr is 0.04 to 0.8:1.

* * * * *